United States Patent [19]

Mazeski et al.

[11] 4,332,566
[45] Jun. 1, 1982

[54] MONITORING ATTENTION AND COGNITION AND THE EFFECT OF SENSORY MOTOR, NUTRITIONAL, AND OTHER BIOCHEMICAL FACTORS THEREON

[76] Inventors: Conrad A. Mazeski; Ken Candelaria, both of 201 W. Prospect Ave., Mount Prospect, Ill. 60056

[21] Appl. No.: 72,328

[22] Filed: Sep. 4, 1979

[51] Int. Cl.$^3$ ............................ G09B 5/00; A61B 5/04
[52] U.S. Cl. .................................... 434/178; 434/258; 434/262; 128/732
[58] Field of Search ............. 35/22 R, 35 R; 128/731, 128/732; 434/178, 255, 262, 127, 258

[56] References Cited

U.S. PATENT DOCUMENTS

| | | | |
|---|---|---|---|
| 3,824,993 | 7/1974 | Grant | 128/25 R |
| 4,008,714 | 2/1977 | Silva et al. | 128/732 |
| 4,028,819 | 6/1977 | Walker | 35/22 R |
| 4,078,319 | 3/1978 | Mazeski et al. | 35/35 R |
| 4,088,125 | 5/1978 | Forgione et al. | 35/22 R X |
| 4,203,452 | 5/1980 | Cohen | 128/732 |

OTHER PUBLICATIONS

*Chemistry of the Amino Acids,* Greenstein et al., 1961, John Wiley & Sons, Inc., pp. 298-311 and title p. (vol. 1).
Pihl, R. O. et al., *Hair Element Content in Learning Disabled Children Science* 198, pp. 204-206, 1977.

*Primary Examiner*—William H. Grieb
*Attorney, Agent, or Firm*—James T. FitzGibbon

[57] ABSTRACT

A method of analyzing learning abilities and disabilities and administering learning therapy to students and other subjects. They are tested for reading ability while their behavior response patterns are being tested by instrumental means including instruments able to detect alpha brain wave patterns and physiological stress, and, where the instrument indicates that the test subject is undergoing a brain wave or stress pattern indicative of brain wave or stress patterns typically manifested by those having learning disabilities, general or specific therapy is administered to reduce the occurrence frequency and duration of high amplitude alpha waves and to reduce the stress patterns within the test subject by sensory motor therapy, print size variation reading therapy and nutritional therapy. The sensory motor therapy includes developing desirable eye movement patterns and sequences by training non-eye muscles and performing exercises in rhythm with reading exercises; the nutritional therapy includes treatment to normalize the amounts and proportions of minerals present in the body of the test subject as well as administering low molecular weight L-amino acids to suppress undue fluctuations in the alpha brain waves of the subject, and the print size variation therapy includes displaying reading matter to the subject in extremely small type during the initial phase of therapy to cause print matter to lie within a reduced angular lateral span and increasing the type size only when the student shows reading improvement.

15 Claims, 17 Drawing Figures

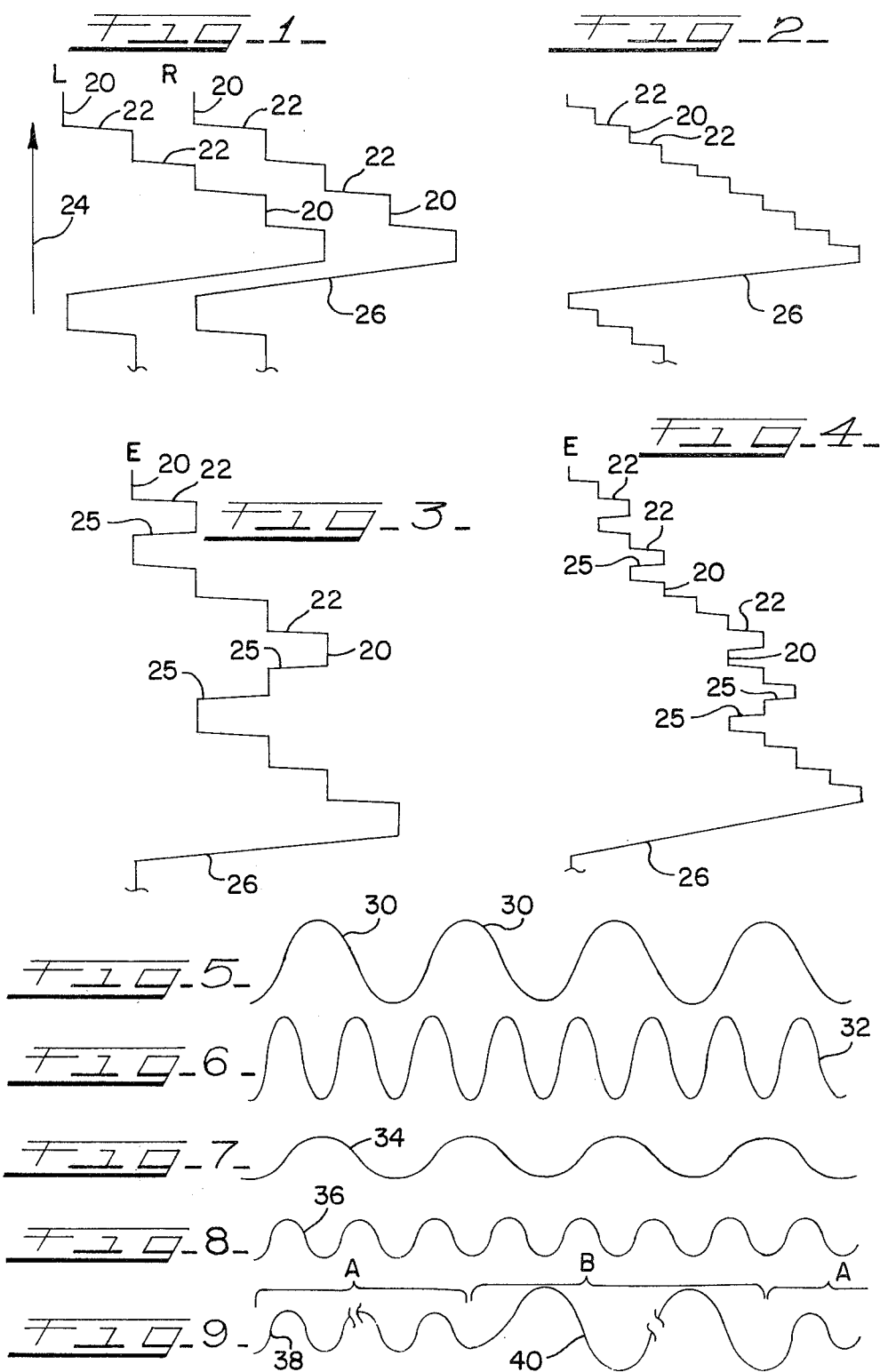

FIG._13_
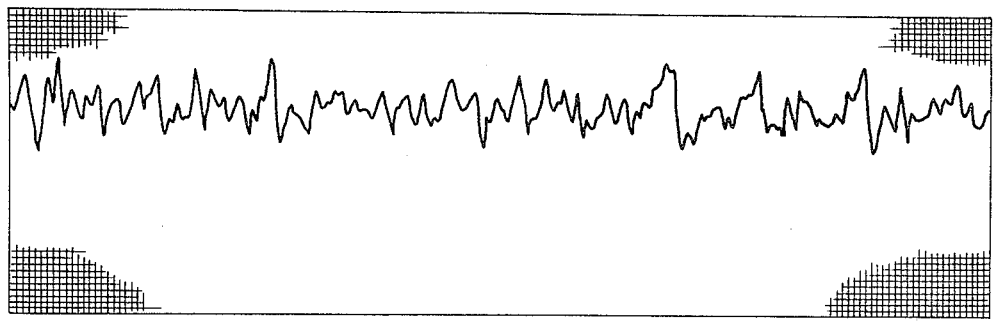
FIG._14_
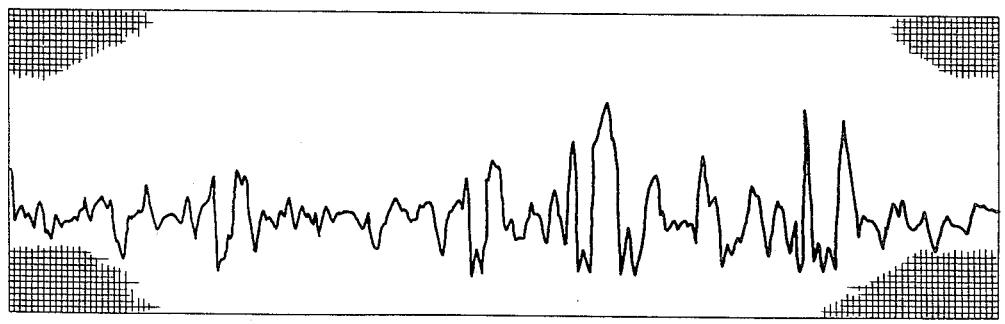

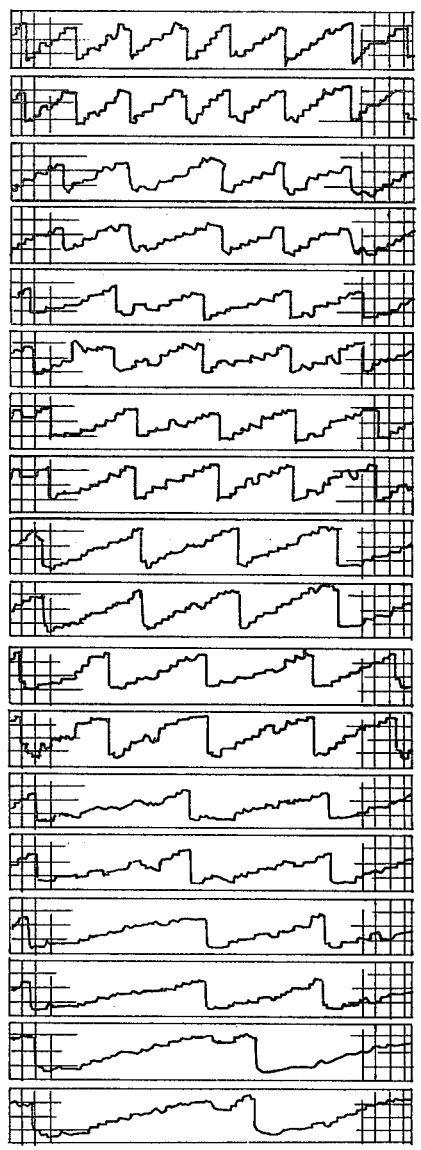
FIG. 15.
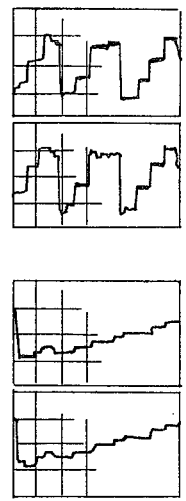
FIG. 17.
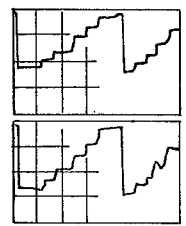
FIG. 16.
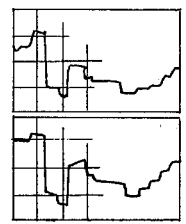

MONITORING ATTENTION AND COGNITION AND THE EFFECT OF SENSORY MOTOR, NUTRITIONAL, AND OTHER BIOCHEMICAL FACTORS THEREON

The present invention relates generally to educational testing, testing methods, apparatus for use in such testing, and interpretation, analysis and management of educational test results. More specifically, the invention is concerned with the teaching and testing of reading skills, with insuring that subjects to be tested are not suffering from physiologically adverse circumstances when being tested, and that persons suffering from physiologically adverse circumstances or conditions have an opportunity to have such circumstances or conditions monitored, and perhaps favorably modified, in the interest of creating favorable learning and testing environments.

Even more specifically, the invention relates to analysis of test subjects by electroencephalographic (E.E.G.) methods to determine brain wave pattern as an indication of attention span and the potential condition for attention, and the application of various other methods, including trace mineral assays, for determining whether the adverse brain wave patterns indicative of predictable learning disability might be corrected by dietary methods and whether adverse physiological effects on brain wave patterns indicative of potential learning disability can be suppressed before the teaching and testing of reading are carried out with a subject. Additionally, myographic and galvanic skin responses are correlative tools to indicate the presence and effect of stress in learning situations. These and the physiological stress evaluation for voice purposes present a comprehensive monitoring system for evaluating the learning (cognitive), sensory motor, and biochemical factors which affect student achievement or progress, and indicate the need for therapy according to the invention.

At present, and referring specifically to lower education, namely, the education of children in kindergarten and through grade or grammar school, there is considerable concern with learning ability, and particularly, the ability of students to read and understand. It is a common practice in schools today to conduct periodically various types of intelligence tests, with such intelligence tests commonly including major portions in which the abilities to read or to attend successfully are controlling or at least very important factors in determining the so-called intelligence quotient or "I.Q." of the subject. Consequently, a person who is unable to attend or to read in an effective manner is severely handicapped in presenting the appearance of having average or above average intelligence as determined by I.Q. tests. According to the present invention, there are at least two distinctly different problems which commonly occur in today's educational process, a major portion of which is intended to be carried out in the public and private schools of the United States.

One such problem is the reliability of an overall determination of the apparent intelligence or I.Q. of individual students within a group of students. Once an I.Q. determination has been made, using generally accepted tests, the student is often classified for further educational purposes, as well as in later life, as being relatively more or less intelligent. Without treating this subject in exhaustive detail, it is generally accepted that people who score poorly on I.Q. tests are forestalled or prohibited from entering a number of desirable jobs or other pursuits. The ability of being admitted to institutions of higher learning, in the case of those having finished high school for example, is determined largely on the basis of I.Q. or comparable tests.

The ability to be admitted into the armed services, to qualify for officer training, to be considered as a candidate for jobs and profession of all sorts, in fact, is often determined by administering intelligence or achievement tests to an array of applicants for a job or profession, and eliminating from consideration those whose scores indicate that they are not particularly intelligent, or are below average with respect to the group from which they are selected or the group in which they would be potentially placed for training.

In extreme cases, and referring particularly to the education of children, many students whose apparent I.Q. is very low are considered by the school systems charged with their education to be slow learners, handicapped learners, or in extreme cases, as persons who are, in the jargon of modern educators, merely "educable" or "trainable".

As pointed out above, a major portion of the determination of the apparent intelligence of a student is based on ability to attend or read, or both. Certainly, a high literary achievement level cannot be attained by one who is not at least an average reader. While a great deal of study has been given to children and others experiencing difficulty with attending and reading, and while repeated attacks on this problem have been made on numerous fronts, there is still a very a large population of persons attending schools of all kinds who are, in a practical sense, unacceptably poor readers. Many person lacking attending and reading skills tend to be classified as lacking in intelligence, and such treatments, unfortunately, functionally doom such children to being considered as having low intelligence and low social desirability during most or all of the entire periods during which they are being educated, and in later life as well.

Recently, as a result of continuing attention to the problem of slow learning, inability to read, inability to attend, etc., it has been discovered that a number of persons who have normal, nearly normal, or in a surprisingly large number of cases, high or even very high intelligence, have, in tests of various kinds, been rated as being of extremely low intelligence.

In extreme cases, persons have been institutionalized, or graded or placed in an educational environment wherein they have been considered as merely trainable or educable, have later been found to have been highly intelligent. Serious consequences of legal liability have resulted, or may result, from such misclassifications. Moreover, the attribute of incompetence has been given to those making such improper classifications. Persons charged with the responsibility of the education of children cannot suffer such charges and attributes lightly.

According to the present invention, methods and apparatus are provided for making a number of preliminary determinations important to making an assessment of intelligence quotient, and particularly, the attention span and reading ability of children.

In one phase of the invention, methods and apparatus are used, including methods and apparatus disclosed and claimed in U.S. Pat. No. 4,078,319, for helping pupils learn how to read. These methods, and variations of these methods, can be effectively used in conjunction with the methods and apparatus of the present invention to diagnose and improve the concentration and reading skills of those who proper diagnosis shows are capable of significant reading improvement if properly analyzed and treated.

Another important aspect of the present invention is direct monitoring a person being tested to insure that the person is in an acceptable or desirable physiological state or condition during the time a reading test is administered. It has been found, according to the invention, that several techniques may be used to accomplish one or both of two important purposes. One such important purpose is to determine whether, as of the time the test is administered, and during the continuation thereof, the person being tested is in a physiological condition which is favorable to his achieving the highest possible score on the test being administered.

Another aspect of the invention is the diagnosis and treatment of persons having problems with attention span and reading-related tests, including intelligence tests, so as to insure that, in the case of persons who are not often in a favorable physiological condition to be tested, their physiological condition can, if possible, be made satisfactory or at least normalized for testing.

In one specific aspect of the invention, it has been determined that verbal comprehension (an aspect of reading ability) depends in large measure on acquired or acquirable skills involving sensory motor coordination. Persons having a high degree of so-called fine motor sensory coordination are physically inherently able to perform, rapidly and repeatedly, the eye movement sequence necessary to successful reading. Even more importantly, persons whose eye movements do not repeaably and regularly follow accepted patterns find it difficult or almost impossible to read satisfactorily.

In some cases, it has been found possible to treat patients having learning problems in such a manner that their sensory motor coordination improves. A portion of this training may be sensory-motor training, as referred to in the patent identified above, it may be training in acquiring an overall sense of rhythmic movement, also referred to in the patent referred to above, or, according to a further aspect of the present invention, it may consist of eliminating hazards or blocks to establishing these sensory motor performances, some of which may be occasioned by what may be considered as either historical or as instantaneous dietary factors.

Further, according to the invention, it has been found that the study of brain waves, while students are engaged in the learning process, and particularly any process requiring concentrated attention such as reading, has revealed information which is very important to an understanding and treatment of students having difficulty with processes such as reading.

Referring now to nutrition or dietary factors, it has been found that a number of students exhibiting chronic reading difficulty may have had such difficulty occasioned by physiological conditions which impaired the ability to attend, and these conditions in turn resulted from poor nutrition. Where such condition has extended over a period of time, and which may thus be considered as historical, it is possible to perform a trace mineral assay on the hair of such person, for example, to determine the relative proportion of minerals which were present in the body of the subject being tested over the period of time in which previous tests were administered.

In many cases, it has been found mineral assays of the hair of such persons indicates that they were deficient in certain minerals in the past, or if not actually deficient in certain minerals, had minerals present in their system in ratios or proportions which were not characteristic of students having acceptable or better reading ability.

For example, by determining the relative percentage of potassium, calcium, sodium, magnesium, zinc, iron, copper, manganese, etc. present in the hair of a person, and making charts of the type which will be referred to in detail elsewhere herein, it can be determined that such percentages or ratios have been proven unfavorable to learning. Consequently, where such unfavorable ratios exist and can be determined, there has literally been an heretofore unknown physiological barrier to acquiring reading and perhaps other learning skills.

According to the invention, dietary modification can be attempted, and in many cases, such therapy can successfully modify the percentages and proportions of such minerals in the body of a subject, with the result that subjects can be made to possess proportions or amounts of minerals in the organic systems which have the effect of promoting concentrated attention required in exercises such as reading. Such subjects then become capable of acquiring reading skills which, under other physiological conditions, they were unable to accomplish.

An important feature of the present invention, therefore, is not only the possibility of changing sensory-motor and nutritional factors of persons having unfavorable mineral ratios as determined by trace mineral assays, but also of insuring that, when a test is administered, these ratios are monitored so that, if they are unfavorable, the test will not be considered truly indicative of the ability of the subject being tested. Consequently, one aspect of the method of the invention involves determining mineral and sensory-motor ratios in the subject, and thereafter engaging in the twofold process of attempting to normalize such ratios by dietary and sensory-motor modifications. The methods also comprehends noting the mineral ratios so that tests taken under conditions where unfavorable ratios prevail may be discounted rather then relied upon, in view of the fact that the mineral ratios may indicate lack of reliability or probity on the part of the test.

A still further aspect of the invention concerns electroencepholographic monitoring of the brain waves of a person taking a reading or intelligence test, and checking variations in results or scores which are wider than those variations normally encountered. In such cases, and also in the case of persons whose test results have shown consistently low scores, but where there is any demonstrated possibility that such tests are not indicative of the true verbal skills of the person being tested, further testing, analysis and/or therapy is indicated. In this connection it has been found that, quite surprisingly, the brain wave patterns of subjects being tested are highly reliable indicators of the attention state of the test subjects.

For those who are able to attend seriously and substantially continuously during the administration of a test, test scores will be truly indicative of the ability of the person. However, in those cases where monitoring, such as EEG brain wave monitoring, can determine that the test subjects undergo fluctuations in brain wave patterns, it can be determined that such persons are not able to attend to the subject matter at hand, or are able to attend only for short periods. In fact, rapid or very frequent brain wave pattern variation is characteristic of what is herein referred to as apparent clinically hyperactive children. Thus, a tester may be testing attention span rather than intelligence, ability, or achievement.

In other words, while clinial hyperactivity is usually considered as being observed behavior comprised of rapid shifting of the attentive faculty from one subject or item to another, it has not always been recognized that the brain wave patterns characteristic of this condition may also be indicative of poor attention leading to reading impediments or disability ("dyslexia").

In subjects who are able to attend for a substantial period of time, ability, achievement, or reading tests give predictable and accurate results. However, if a test is administered to a child who is able to attend effectively only one-half or one-third of the portion of the time during which the test is being administered, such child will almost certainly receive a poor test score. Where such apparent hyperactivity is able to be cured by treatment according to the invention, or where such activity is not a common condition, but occurs during class activities or testing, then it is important to know the physiological condition of the subject at the time of the classroom activity or test so that, at the least, the test results obtained will not be relied upon as being truly indicative of the ability of the subject being taught or tested.

Reactions to substances such as foods or liquids which can affect learning, and sensory motor or visual motor factors may also be tested by electronic monitoring of the attention span.

These reactions affect brain activity and subsequent attentiveness which, of course, affect learning, particularly reading. For example, addition of foods containing salicylates may impede the progress of learning as evidenced by erratic oral reading while the individual is being monitored after ingestion of a salicylate-containing food item. Prior monitoring which indicates a high attention level before salicylates intake is used to compare wave frequencies and amplitudes for diagnostic purposes.

According to the present invention, certain known methods are used to develop and improve attending and reading skills of test subjects, while certain other novel discoveries are used in conducting testing as well as analyzing reading test results with the view towards insuring that such results are not considered indicative of the ability of the student where any one or more of a number of indicators are present that the test subject is suffering from a physiological abnormality or insufficiency which affects his ability to perform well in the classroom or on a test.

In further keeping with the invention, once the nature of the learning disability has been determined, specific measures can usually be taken to insure that testing is more accurate, and in many cases, that the ability to read, attend and consequently, the ability to achieve higher I.Q. and other test scores can be accomplished.

In view of the foregoing, and in view of the difficulties and inaccuracies associated with prior art teaching and testing methods, it is an object of the invention to provide improved methods and apparatus for diagnostic testing.

Another object of the invention is to provide a testing method which decreases the likelihood that test subjects will be improperly or inaccurately classified.

Another object of the invention is to provide a method of testing, particularly a method of testing for reading skills, which is of improved reliability with respect to prior art methods.

A still further object of the present invention is to provide improved methods and apparatus for monitoring subjects for attention span during the times various tests, including reading tests, are being administered to the subjects.

Yet another object of the invention is to provide methods of insuring that a subject being given a test presents a favorable physiological condition during the time the test is administered, and in some cases, to insure that such person maintains such a favorable physiological condition during testing and thereafter.

Another object of the invention is to provide a method of determining whether previously administered tests are valid or invalid as indicators of the ability or the intelligence of a subject being tested.

A still further object of the invention is to provide a method of testing which includes monitoring the brain wave functions of a subject being tested to determine the amplitude and frequency of the brain waves, which in turn can indicate the ability of a subject to attend to or focus his attention on the subject matter of the test.

Another object of the invention is to provide a method of analyzing minerals present in the subject being tested to aid in determining whether, at the time the test was administered, the subject was suffering from a diagnosible mineral deficiency or imbalance.

A still further object is to provide a method of determining or predicting whether a mineral deficiency or imbalance can be remedied so as to physiologically increase the likelihood that a test subject will produce a better or more reliable test score.

Another object of the invention is to provide apparatus and methods for determining a base or typical physiological condition of the test subject so that an accurate indication may be had of the reliability of subsequently administered tests.

Yet another object of the invention is to provide methods and apparatus for discriminating among test subjects and predicting the nature of the learning behavior of such subjects by the use of the testing method of the invention.

A still further object is to determine which students, among an arrary of students, will be able to be helped in their learning ability by the application of specific dietary practices, rhymthic training, the use of negative power or minifying lenses, or other applications of established reading improvement technology so as to measurably increase their actual reading skills.

Another object of the invention is to provide testing methods and apparatus which will insure that a test subject is not misclassified as a result of administration of an important test under improper conditions.

A still further object of the invention is to use electroencephalographic methods to monitor the brain wave activity and consequent attention span or attention behavior of subjects being tested.

An additional object is to develop useful further test criteria which include the development of a quotient relating indicated I.Q. and the sensory motor response level of an individual being tested.

It is also an object of the invention to provide a method of discrimination between so-called visual attention, auditory attention, multiphased attention, and visual learning only, with such states being determined by definition of the type of measurable brain wave activity occurring during testing administered to the subject of such tests.

Other objects of the invention include developing and using improved methods of preparing a subject for testing, methods of analyzing test results to determine whether the test results are indicative of the information believed to be obtained by such tests, and an avoidance of erroneous or questionable classifications of test subjects.

The foregoing objects and advantages of the invention are achieved in practice by providing a method which includes monitoring brain wave activity while subjects are being tested, and comparing such activity with a desired or standard activity as a means of determining the physiological state of the subject during the time the test is administered. The invention also achieves its objects by providing methods, including trace mineral assay methods, of determining the mineral content of the subject prior to or after testing, and comparing such mineral assays test results with predetermined standards to determine whether information developed during testing has apparent reliability. The invention also achieves its objects by indicating the desirability of providing dietary modifications to persons susceptible of unfavorable brain wave activity before, and after testing, so as to increase the accuracy, reliability and reproduceability of the tests being administered. The invention achieves other of its objects by improving and controlling the conditions under which reading and reading improvement are taught and tested in an academic and/or clinical atmosphere.

Still other objects are achieved by using additional testing, monitoring and/or training equipment, including voice stress analysis equipment used during oral reading or recitation, sensory motor training equipment, including apparatus for developing homolateral and cross-lateral gross motor movement patterns, skin condition monitoring equipment including electromyographic equipment, skin temperature detection equipment, and dermomographic or skin conductance and skin potential detecting equipment. This and other equipment may be used in the process of determining whether conditions favorable to maintaining close attention are being, or can be, maintained in the suject who is attempting to learn or who is being tested.

The exact manner in which the invention achieves the foregoing and other of its inherent objects and advantages will become more apparent when reference is made to the following detailed description of the preferred embodiments of the invention set forth by way of example, and to the accompanying drawings, wherein like reference numbers indicate corresponding parts throughout the several figures.

BRIEF DESCRIPTION OF THE DRAWINGS

FIG. 1 is a representational view of an eye movement tracing indicative of the eye movement undergone by a skilled reader and showing the movement of left and right eyes during the reading process;

FIG. 2 is a diagrammatic view of the eye movements with time, but representing both eyes and showing the eye movements of a relatively unskilled but acceptable reader.

FIG. 3 is a view similar to that of FIG. 2 but showing the eye movement or tracing undergone by a person reading rapidly but unskillfully and showing regressive movement.

FIG. 4 is an eye movement trace of a slow, unskilled reader;

FIG. 5 is a diagrammatic view of the alpha brain waves as determined by an electroencelphlograph and showing a steady state, low attention condition;

FIG. 6 is a view similar to that of FIG. 5 but showing a brain wave of somewhat higher average amplitude;

FIG. 7 is a diagrammatic view showing the brain waves of a person during a state of attention;

FIG. 8 is a diagrammatic view similar to that of FIG. 7 but showing the person whose brain wave pattern is characterized by a somewhat higher average amplitude; and FIG. 9 is a diagrammatic view, with portions broken away, showing the brain wave pattern of a typical problem reader whose brain wave pattern fluctuates between attentive and non-attentive states, and whose treatment can be achieved for improvement according to the invention.

FIG. 13 is an actual brain wave pattern showing a pattern trace showing a person in a state of attention such as that shown in FIG. 12, but displaying a somewhat higher amplitude wave;

FIG. 14 is a photoprint copy of an actual trace of a brain wave pattern of a problem reader, showing a pattern of fluctuation between attentive and non-attentive states, with such pattern characterizing a person whose brain wave pattern can typically be improved when the subject being tested is treated according to the invention;

FIG. 15 is a photoprint copy of a series of graphs showing typical eye movement patterns of reading subjects from first through eighth grade levels, through grade eleven, and into college, and showing gradual improvement in the reading performance of the subject as reflected by the characteristic pattern of eye movement;

FIG. 16 is a photoprint copy of a pair of eye movement charts showing a poor directional attack on reading matter in contrast to a good directional attack; and FIG. 17 shows a pair of eye movement graphs illustrating the contrast in patterns between an inefficient reader and an efficient reader.

DESCRIPTION OF THE PREFERRED EMBODIMENTS OF THE INVENTION

Figure 10:
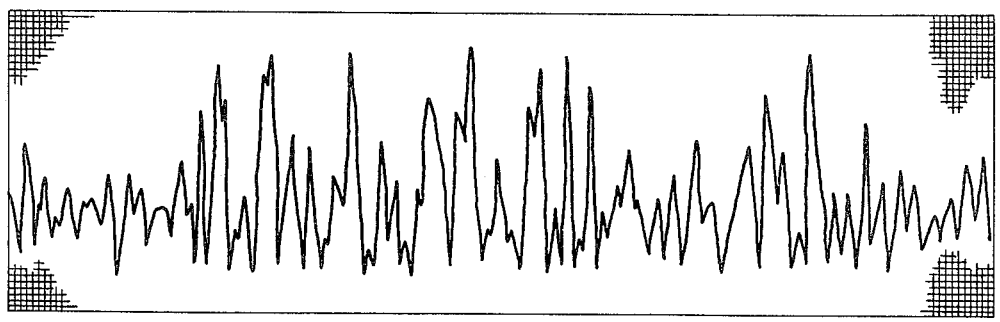
FIG. 10 is a photoprint copy of an actual trace of a brain wave pattern, taken during a time that the test subject was in a condition of low attention.

While the methods of the present invention may be practiced in various ways, while such methods include a number of apparently different aspects, and while several steps may be omitted in the performance of certain of such methods, a description of several preferred embodiments of the invention will be made by reference to particular problems which have occurred, with examples being given of the manner in which such individual problems have been treated and resolved according to the invention.

While the principles of the invention can be demonstrated with groups having more advanced reading skills, it is generally possible to obtain greater improvement in reading ability when dealing with children in the lower grades rather than with older children, and therefore, younger children were used to demonstrate the invention. Accordingly, a group of twenty-three (23) students taken from kindergarten through fifth grade were given an initial diagnostic or screening test.

Upon testing such an array of children selected from these grades, it was determined that a very significant portion—nearly 40%—of the school population demonstrated so-called observable visual regressions while reading, and about 15% demonstrated severe or excessive observable visual regression.

Referring to the drawings, FIGS. 1-4 show typical traces of pupilary movements of the eyes of various subjects during reading. While a detailed explanation of the drawings appears below, it is believed helpful first to consider the eye movement process of various types of readers.

Specifically, a highly skilled reader will encompass several words with a single glance, comprehend these words rapidly after a short but measurable, finite time, then move his eyes together as a unit to the next group of words on the right, and so on, until a line has been read, then shift his eyes downwardly to the next line and repeat the process.

Slower readers perform the same movement sequence, but take in a smaller number of words in each glance, that is, their eye span, measured laterally, is reduced in respect to that of good readers.

Poor readers, regardless of their eye span, however, read one or more groups of words, then undergo a backwards or left-moving glance to reread certain preceeding word or groups of words.

Typically, a reading eye camera is used to determine the exact eye movements of a reader. In one typical form of such device, a beam of light is directed onto the pupils of the reader, and light reflected therefrom is directed to a photographic film strip which moves at a constant speed. Consequently, a trace of eye movement such as those shown in FIGS. 1-4 will show vertical and nearly horizontal lines. Referring specifically to FIG. 1, there is show left and right traces "L" and "R", with each trace including a series of vertical lines 20 spaced apart by a series of nearly horizontal lines 22, with the movement of the strip chart being indicated by the arrow 24. Thus, with the film strip moving in the direction shown by the arrow, after the eyes fix upon a portion of the material to be read, they remain there for a predetermined time necessary to absorb the information. Thereupon, the eyes fix upon the next word or array of material to be read. Thus, the vertical line shows that the eye remain fixed for a period, while the line 22 shows that the eye moves to the right. The line 22 slopes slightly down to the right, denoting passage of only a short time during this rapid eye movement. As will be noted, in FIG. 1, the eye movements are the same for the left eye as for the right eye, with the left eye movements being shown in the area L and the right eye movements being shown in the trace or pattern R. Consequently, only a single trace is shown in FIGS. 2-4.

FIG. 1 shows eye movements of an excellent or fast reader. Because a larger lateral span is comprehended by the reader, only five eye fixations are shown to be necessary to read a line of a given width. FIG. 2 shows ten eye movements as being necessary to read the same material, it being understood that this test subject would be reading the same material.

Referring now to FIG. 3, the eye movements associated with a somewhat rapid but an erratic reader are shown. Here, there are horizontal areas 25 moving back to the left, between lines, followed by subsequent movements 22 to the right. By reference to FIG. 3, it will be seen that the reader, in attempting to read with eye movements of this type suffers from a serious handicap. First, the reader, instead of progressing through the material in sequence, has stopped and gone backwards, consequently losing a certain amount of time. Moreover, after one or more backward movements, the reader invariably re-reads the immediately following material, and as a consequence, is forced to read much of the material twice. In extreme cases, sometimes even three or four rereadings are necessary because of numerous regressive movements.

FIG. 4 shows the eye movement trace of a student who reads as slowly as the reader of FIG. 2, and who also has the frequent regressive movements of the reader of FIG. 3. In all figures, the line 26 is a return sweep movement to start the next line, and hence is not considered a regression.

As has been determined in speed reading and other studies, such movements not only slow down the reader, but cause lack of understanding and confusion, because, by the mere physical act of re-reading the material, the orderly sequence of the material is also lost to the reader. It has been demonstrated beyond question that fast readers comprehend and retain more than slow readers. The reason is believed to be that the slow readers read erratically and thereby fail to determine the sense of the material which consists in the arrangement of the words and phrases as well as their mere presence in the reading material.

One reason for failure of orderly eye movement sequence is that the reader has not paid attention to a particular bit of reading information when his eyes are directed to it. Consequently, after one or more rightward moves with the eyes the reader becomes aware, consciously or otherwise, of the fact that his attention has failed, or that he did not comprehend the meaning of an earlier portion of the line of words he is reading. Thereupon, his eyes undergo backward or regressive movement. With the passage of time, this conduct becomes habitual and has extremely adverse consequences on reading ability. In many cases, including those with which the invention is concerned, the failure to attend results from a physiological cause which can be helped by dietary methods, or in other cases, from psychological and physiological causes which can be remedied by training, as will appear.

According to the invention, children selected from the array referred to above and characterized by difficulty in the reading process were treated, according to the invention, by training so as to develop or improve the general innate rhythmic sense of the body. Still further, material being read was presented to the reader with negative dioptric power (minifying) lenses. In this connection, reference is made to the methods and apparatus described and claimed in U.S. Pat. No. 4,078,319. Briefly stated, such patent refers to the concept that the body of a child may be made to develop and express a rhymthic sense, and develop what may be considered analogous to a metronomic function by the snapping of fingers, squeezing a bean bag, ball, or the like in rhythm with the intended movements of the eye. This in combination with the use of negative power or minifying lenses helps significantly decrease the incidence of visual regression. The use of the minifying lens is helpful because, contrary to prior art beliefs that much reading difficulty can be cured by magnifying the object to be viewed and causing it to lie within an area of larger angular lateral span, minifying or making the object smaller causes the reader or other observer to narrow the lateral span of his gaze and consequently to increase the attention brought to bear on the matter to be read.

Consequently, persons without gross physiological or nutritional impediments to learning can have their reading skills substantially increased by the use of these methods. However, certain children whose reading skills can be improved as just described still show occasional or even frequent lapses into times of poor reading, and according to the invention, it has been discovered that this can often be traced to otherwise asymptomatic dietary difficulties.

Referring now to a demonstration of this aspect of the invention, FIGS. 5–9 show plots of various brain wave patterns taken within an E.E.G.

FIG. 5, although shown without any particular numerical indicia, is intended to represent so-called alpha waves characteristic of a subject during waking hours. Alpha waves are generally considered to be those brain waves having a frequency of up to about ten to eleven cycles per seconds (cps). Characteristically, when brain wave cycles have the large amplitude of the waves 30 in FIG. 5, the subject is in a non-attentive state.

FIG. 6 shows a similar tracing, but the characteristic wave form 32 is typical of an older person, and consequently, while the amplitude is still large, the frequency of these waves is somewhat higher. In this connection, adult brain wave patterns sometimes reflect frequencies of ten to eleven cps while children, particularly those in a non-attentive state, may develop brain wave frequencies of five to eight cps, for example.

Referring now to FIG. 7, a very low amplitude wave 34 is shown. This wave is a typical brain wave pattern detected when the subject is in a state of relatively close attention and thus in a state wherein he is susceptible to significant reading comprehension. FIG. 7 shows a low amplitude wave but this wave has a frequency corresponding to that of FIG. 5.

FIG. 8 shows a pattern 36 which is also typical of a highly attentive state and which has a frequency approximately corresponding to that of FIG. 6. FIG. 7 would be a typical brain wave pattern taken from a child who was a good reader during the time he was reading and attending closely while FIG. 8 is an illustration of a typical brain wave pattern for an adult who is in highly attentive state and wo is, therefore, susceptible to learning.

FIG. 9 is an illustration of a mixed brain wave pattern having a plurality of low amplitude segments A and a plurality of high amplitude segments B.

This figure illustrates that it is possible for the subject, during the time his brain wave activity is being monitored, to change between states of relatively high amplitude and those of relatively low amplitude. As pointed out above, because a high amplitude state is inconsistent with the attention required to read successfully, tests taken or reading attempted during a period of high amplitude brain wave activity almost always indicate that the person cannot successfully read and comprehend the material being considered and, according to the invention, this indicates that steps should be taken to determine whether the subject has a physiological or other involuntary reason for such pattern.

Referring again to FIG. 9, the portion 38 of the wave line within region A and the portion 40 line within Region B are shown to be separated to illustrate that the number of cycles of each typical activity undergone may be only afew or up to dozens or perhaps hundreds of cycles. However, when the shift between low and high amplitude states occurs, several times in a second or every few seconds, it has been found that it is almost impossible for such a person to comprehend reading matter successfully. A brain wave of the type shown in FIG. 9 is a pattern which is also typical of diagnosed clinically hyperactive child. However, the term "hyperactivity", in this connection, refers not literally to the movement of the child but to his short and/or erratic attention span.

Reference will be made herein to methods and apparatus for controlling or altering the brain wave function of a subject, or at least observing it during testing so as to obtain an indication of the reliability of the test being administered.

Referring now to the administration of such tests, as is known to those skilled in the art, the EEG readings are taken by placing the electrodes near the striate or visual cortex area, that is, the occipital area, of the brain. FIGS. 5–9 show brain waves for purposes of illustration. However, in the preferred form of practicing the invention, rather than attempting to observe and interpret a continuously occurring brain wave, a form of EEG is used which has a digital readout.

In such case, the read out averages the frequency and amplitude of the brain waves. After a base value is established for each subject, the subject is then observed during an attempt at reading—and the nature and extent of deviation from a standard state is noted.

In this connection, with an integrator type of read out, the numerical values are average values of frequencies and amplitude. That is, for example, if the subject were not in an attentive state, he would have an amplitude value of ten, and if the amplitude for an attentive state were two, a subject whose brain waves were at the ten level half the time and the two level during the other half of the time in question would have an average amplitude of six. Consequently, if, during reading, the values of two and ten were developed, a reading of five, six or seven would show that the subject was in a very inattentive state, intentionally or otherwise, and consequently, his test score should not be taken as indicative of a performance which he could be expected to give were he in a highly attentive state characteristic by an amplitude of two or three. If such subject were capable of achieving a two level during high concentration activity and actually achieved a 2.5 level during testing, a determination could be made that it was not perfectly attentive, but a value would show that his lapses into an inattentive state were only occasional or periodic rather than frequent and/or regular.

In the practice of this aspect of the invention, a subject was selected and the electrode of the EEG was attached to him as described above. The EEG values were then observed, while the subject was examining reading material. After having an opportunity to study the reading material, he was tested by standard methods, such as the Iowa test or other test known and accepted in the profession. By testing the subject and observing the correlation between his ability to attend and to learn from reading material and the characteristic brain wave manifested, it was discovered, quite surprisingly, that his alpha waves characteristically were in a low amplitude condition, while the subject was in fact attending to the written material and therefore had the required opportunity to learn therefrom. When the attention of the subject was wandering, or he was unable to attend to the subject matter of the reading test, the alpha wave values were characteristically very high.

Extended study of brain wave tracings also indicated that where there was a rapid transfer between the two brain wave states, i.e., a rapid fluctuation between states of attention and lack of attention, the behavior of the subject is typically that of a hyperactive child having a short attention span and consequently a diagnosed, so-called learning disability.

Once a correlation between the typical hyperactive behavior and the brain wave pattern was established, it was then possible to determine whether methods or apparatus could be used to alter the brain wave pattern of the subject for purposes of increasing his susceptibility to developing successful reading habits, and consequently to learn through reading and thus be considered more intelligent.

In addition, it was able to be determined whether certain persons exhibited adverse brain wave patterns during testing and, in the case of persons who frequently exhibited such patterns, it was able to be determined that the tests were unreliable as indicators of maximum reading ability and consequently maximum intelligence which the tested subject is capable of manifesting and being tested for.

Next, discrimination or diagnosis of causes of brain wave pattern irregularities was undertaken. In this connection, there were those whose brain wave patterns could be made to fluctuate instaneously and those whose brain wave patterns could be altered over a period of time.

In one experiment, a subject being tested and who displayed questionable or inconsistent brain wave patterns was connected to the EEG machine and brain wave patterns or values were recorded. After a base line was established, the person was fed one teaspoon of processed white sugar. Immediately, in fact within two to three seconds, the brain wave pattern of the subject changed, even though there were no other apparent indications of reason for such change. The application of sugar to the blood stream of this person was thus seen as an indicator that dietary variations are capable of changing brain wave characteristics on a substantially instantaneous basis. From these data, it was possible to determine that in the case of persons having low test scores, the scores should be regarded as possibly unreliable, particularly where the children had eaten before the test or were permitted to eat during the test.

After having determined that certain dietary materials, such as the sugar referred to above, were capable of causing drastic alterations in the brain wave patterns, a determination was attempted to be made whether the adverse effect of dietary intak could be counteracted or suppressed within the tested subject. According to the invention, it has been discovered that certain L-amino acids, when administered to the subject, were capable of suppressing the reaction which was indicated when the subject was fed the sugar product referred to above. So-called M 2 Singular Free form simple L-amino acids include L-valine, L-leucine, L-isoleucine, L-threonine, L-lysine, L-cystine, L-methionine, L-phenylalanine, L-tyrosine, and L-tryptophan.

After a number of subjects had been identified whose brain wave patterns were susceptible to sugar-induced fluctuation during testing, the subjects were given what are referred to herein as "brain wave variation suppressor agents", (the above amino acids in this case) and then tested. The brain wave patterns then remained much less random during testing, and consequently, higher indicated test scores were able to be achieved by subjects of this type, it being thereby concluded that a tested subject who might be adversely influenced by improper dietary factors would produce test results more indicative of his true mental state and ability, or potential therefor, if the dietary substances inducing adverse brain wave patterns were eliminated or controlled.

As a result of the foregoing, it has been determined that many persons believed to have low reading ability can be referred to skilled nutritionists, who in turn can establish control over adverse dietary factors, and, in some cases, develop eating habits favorable to the production or maintenance of brain wave patterns favorable to receptive reading.

Reading improvement techniques can then be applied to such individuals, who can thereafter be tested and shown to display a rapid, and in some cases dramatic, improvement. The reading improvement programs include the use of negative power or minifying lenses, and rhythmic training and frequent checking of the visual regression patterns of such persons. In certain particular cases, subjects given this treatment were able to advance up to one full grade reading level in less than four months, and virtually all of the subjects tested displayed significant and sometimes dramatic increases in their ability to read.

Referring now to certain other subjects being tested, namely, certain of those who displayed either chronic or occasional irregular brain wave function, or, even when not so measured, an apparent inability to acquire reading and related learning skills generally, a number of students not otherwise demonstrating apparent physical reasons for learning disorders were analyzed according to the invention. The scalp hair of these students was analyzed by the trace mineral assay method of a type known to those skilled in the art, and described in the literature referred to herein.[1]

1. See bibliography contained in Appendix hereto.

As brought out in this literature, the hair of a subject, which continues to grow, may be thought of as a dietary history of physiological conditions within the subject. For example, if a person is given foods containing certain minerals over a period of time, and then such foods are withheld from the diet, the hair of such subject can be analyzed and different regions lying within the entire length of the hair will be shown to be characterized by a heavy concentration of such mineral in certain areas and a lighter concentration in others. Thus, the hair may be thought of, for this purpose, as analogous to a recent nutritional history of the person.

According to the invention, the gross amounts of minerals present in the hair, as well as the proportions of minerals with respect to other minerals can be analyzed. When this is done, charts or standards can be prepared which indicate the normal range of variations in mineral concentrations as well as excessive ranges not only in absolute quantities but in proportions in relation to each other.

Among the minerals tested for are metals, such as calcium, magnesium, zinc, iron, copper, sodium, potassium, lithium and maganese. Other metals which are actually toxic, if present in the subject, may cause symptomatic learning disability. These metals are also specifically tested for in keeping with the present invention. If their presence is detected by one means or another, some action must be taken to eliminate their presence in the subject. These metals include lead, cobalt, aluminum, cadmium, mercury and, to a lesser extent, barium.

In one of the studies referred to in the bibliography, the authors reported obtaining 98% accuracy in determining the existence of learning disabilities in children based solely on the study of hair trace mineral assays. The authors used an analysis of cadmium, cobalt, maganese, chromium and lithium. However, no curative therapy was postulated, no possible improvement of visual motor function was discussed, and there was no expression of a possible relation between normalizing the values found in the assay and improvement in visual motor function.

Once a trace mineral assay has been made on a subject, and the subject displays abnormalities in the ratios referred to herein, in most cases, sensory-motor and dietary therapy, particularly in the case of school children having reasonably controllable adult home supervision, can be undertaken with the object of restoring balances which are shown to be desirable in the sense of falling within the amounts and ratios characterizing healthy children free from reading disabilities.

When such programs are conscientiously carried on, the change in the mineral balance of the subject can be validated by assays. In the meantime, according to the invention, it has been shown that consistent and in some cases intensive reading training can be applied to an individual child with far greater success than would have been able to be achieved in the absence of dietary modification. The exact minerals to be furnished to such subjects, and the foods in which such minerals are abundantly contained, and, in general, the manner of administration, is not necessarily a part of the invention which is novel per se, and in any case, is that which can be undertaken and achieved by a nutritionist having before him the mineral assay information referred to herein. Accordingly, the exact manner of altering sensory-motor activities by diet and ultimately achieving change of mineral balance will not be discussed in detail herein.

According to the present invention, the ratios of minerals which should be present in the hair are set forth below in tabular form:

| Ca to Mg | Ca to Zn | Ca to Fe |
|---|---|---|
| 7.5–8.5 to 2 | 3 or 4 to 1 | 11–12 to 1 |
| Mg to Zn | Mg to Fe | Mg to Cu |
| .3 to 1 | 1.5 to 1 | 1.7 to 1 |
| Na to K | K to Fe | K to Zn |
| 2 to 1 | 3.2 to 1 | .2 to 1 |
| Zn to Fe | Zn to Cu | Fe to Cu |
| 8 to 1 | 5 to 1 | 1 to 1 |
|  | Mg to Mn |  |
|  | 14 to 1 |  |

Absolute values of the minerals referred to above may also be determined and used for analytical purposes. A table of values is not reproduced herewith, however, inasmuch as desirable absolute values are already known to those skilled in the art, and further, because such values vary considerably, although within established limits, depending on the age and sex of the subject.

According to the invention, variations from the values set forth above and variations from the ratios set forth above may be indicative of learning or reading disability, or at least indicate that the subject is capable of undergoing significant learning or reading improvement when the ratios have been normalized or brought to the approximate values and ratios set forth above. Deviations of as little as 10 to 20 percent from the above values are sometimes significant, but in many cases, the values are much further from the preferred ranges set forth above.

Individuals, particularly children, showing dyslexic tendencies, poor or short attention spans and so-called hyperactivity should be subjected to an analysis of the alpha brain waves using an EEG, preferably one with a digital readout. When it is possible to suppress the alpha waves by reducing the amplitude thereof, and entering the beta wave state, a more attentive posture can be attained and the student is more subject to reading improvement.

Suppression of high amplitude alpha waves may also be achieved by the use of the amino acids referred to herein. Such acids may be administered as a form of "insurance" against unexpected increase in brain wave amplitude if desired, but their use may often be definitely indicated where the dietary factors indicate that high amplitude brain waves are occurring frequently when the subject should be in a more attentive state characterized by lower amplitude waves.

The use of negative power dioptric lenses also suppresses the alpha waves as do specific sensory motor activities, particularly those which can be made habitual within the student. The method of the invention uses the specific sensory motor activities such as the cadencing referred to in U.S. Pat. No. 4,078,319, the negative power lenses referred therein, but also with the immediate and long term dietary modification referred to herein.

When the alpha waves are monitored, the longer the suppression, and the more cycles per second, the longer the indicated span of attention. A long attention span is an accurate predictor of success for children or adults, particularly those needing reading improvement, it being assumed that the ones having excellent reading habits would not be in reading assistance programs.

Tests of the type known to those skilled in the art, and referred to as sensory motor reponses or response tests, particularly those relating to fine sensory motor activities, must be developed for a reader to be successful. The overall ability of a person to develop fine sensory motor responses is a predictor of his ability for reading skill, inasmuch as fine muscular movements of the eye are analogous to other fine muscular movements required and able to be tested by sensory motor response tests. A quotient between the indicated I.Q. and a sensory motor quotient can be used to screen individuals requiring further alpha wave patten monitoring. Children showing wide variances between I.Q. and sensory motor activity ability should be made the subject of careful study.

While it is virtually impossible to teach a person with poor fine motor skills, e.g. poor visual motor response, how to read well and how to learn from written material, where such person is capable of improving his visual motor function, such person is likewise capable of significant or dramatic increases in learning ability generally and specifically, in reading ability. According to the invention, many persons now having poor visual motor function are able to improve their visual motor function considerably by optical exercises, other physical exercises, particularly rhythmic or cadenced exercises, by dietary modification and by other therapy referred to herein. Still further, the effects of such therapy can be monitored by analyzing the brain wave function of the subject.

It has been found that a number of persons having potentially good visual motor function do not achieve the reading or other learning skills of which they are theoretically capable. With such persons, the problem lies in intermittent lapses into poor visual motor function, or temporary failure of such functions because of stress factors, dietary factors, etc.

According to the invention, the visual motor function in such people can be improved in quality, and/or steps can be taken to insure that important tests are not administered to such subjects and relied upon, if, at the time the tests are taken, the subject is displaying instantaneous indication of poor or erratic fine motor skills, and particularly, poor visual motor response.

All persons suffering from apparent learning disability should have a brain wave monitor taken periodically in conjunction with the status and progress of their reading improvement program. The trace mineral assays serve as free standing indication that dietary or other physiological health care is definitely indicated.

Referring briefly to brain wave studies, while certain amount of suppression in alpha wave amplitude is desirable, extreme suppression of alpha waves and increase in beta wave activity tend to indicate that the person may be one who learns only by seeing or reading rather than by hearing, etc. and in this case, alternative learning methods may be indicated for some students having extreme values in tests of this sort.

Of the group of 23 students referred to above, those with some visual regression, about half were able to accommodate reading rather well while the other half found reading quite laborious. Of those demonstrating excessive or frequent visual regressions, over 90% had great difficulty with reading. The use of minus lenses helped to control visual regressions in those children whose regressions were not initially excessive. Where a program of cadencing and rhymthic instrumentation are used, it is also possible to control erratic eye movements, as referred to in U.S. Pat. No. 4,078,319 and elsewhere herein. The control of sensory-motor activities and diet and the addition of dietary supplements, such as vitamins and minerals can be helpful, particularly if there is parental cooperation, which includes meetings between the reading therapist, nutritionist, dietitians, and physical educator or therapist. The validity of such therapy is indicated because, under clinically controlled conditions, better and more consistent improvement is found with children whose sensory-motor activities and diets could be carefully supervised.

In validating these studies, made by the Iowa Test of Basic Skills, another study was made which involved the use of the so-called Gates Reading Test, i.e., tests wherein the student is not timed for speed. Children taking this test and given the therapy provided by the present invention were able to improve reading significantly and in some cases, averaged close to two years reading progress within a three month span using the minus lenses, nutritional information, and the sensory-motor exercising programs. The basic features of the present invention include the cadenced reading program using minus lenses, a neuromuscular rhythmic exercise program and the derivation and use of information about nutrition so that the child's reaction times and total coordination patterns can be improved by implementing such information both clinically and through advice to parents and observation of children from the classroom teacher's view.

Referring to correlating the data on which the conclusions of the present invention are based, it has been proved that children who score higher on non-verbal than verbal tests generally have erratic visual or neuromuscular control mechanisms, making effective reading difficult or impossible. Children whose parents and/or teachers feel the student "seems" normal or even bright, but cannot read well, are usually those having mechanical problems, that is, erratic visual or neuromuscular controls. The ability to read presupposes a development of fine motor skills.

Referring now in detail to certain of the drawings, whereas FIGS. 1-4 show schematically developed illustrations of reader's eye movements, FIGS. 15, 16, and 17 show actual traces made using a reading eye camera. Referring specifically to FIG. 15, it is shown, on the left thereof, that in order for a student to traverse one line of print, a large number of eye movements are made and there is a significant vertical space between right-to-left or return sweeps of the eyes. In the chart height indicated, only two such movements are seen in the eyes of a first grade reader. A second grade reader has three such movements shown, as does a third grader.

The eye movement progression, although regular, is obviously laborious, and is characteristic by many glances within a single line. On the right of the graph, where eleventh grade level and college grade level student eye movement sequences are shown, about six to eight return movements are shown, indicating that the college and secondary school reader reads the same material with many fewer eye movements and reads six or seven lines in the time the first grader reads two lines. Gradual progress is evident in grades two through eight and continuing into high school. In almost all of the reading patterns shown, there is frequent regression, which is undesirable. This illustrates that even good readers may lapse into momentary inattention, and are capable of further improvement in their reading patterns and habits.

FIG. 16, in Part A, shows an eye movement sequence typical of poor so-called directional attack. That is, the eye movement is almost entirely random. FIG. 16 shows good directional attack with no regressive movements.

FIG. 17, Part C, shows a slow, inefficient reader whose eye movement pattern shows long fixation and many movements per line. The reader whose eye movements are traced in Part D of FIG. 17 reads three lines while reader C reads one line. His eye span is greater and his dwell or fixation time is greatly reduced.

Figure 11:
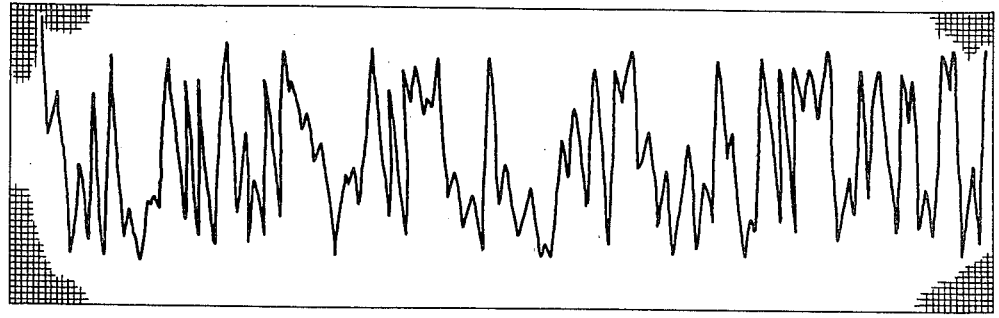
FIG. 11 is a photoprint copy of an actual trace of a brain wave pattern, showing a person in a state of inattention and showing the brain wave having an even higher amplitude wave than that shown in FIG. 10.

Referring now to FIGS. 10 through 14, these illustrations show actual brain wave patterns taken with a strip chart recorder. FIG. 10 corresponds to the schematic illustrations of FIGS. 5 and 6, as does FIG. 11. FIG. 11 shows a very high amplitude, highly erratic trace with almost no attention, while FIG. 10 shows some areas of moderate amplitude. In this respect, FIG. 10 also resembles FIG. 9, which shows an area "A" of relatively high attention, interspersed between areas "B" of low attention.

Figure 12:
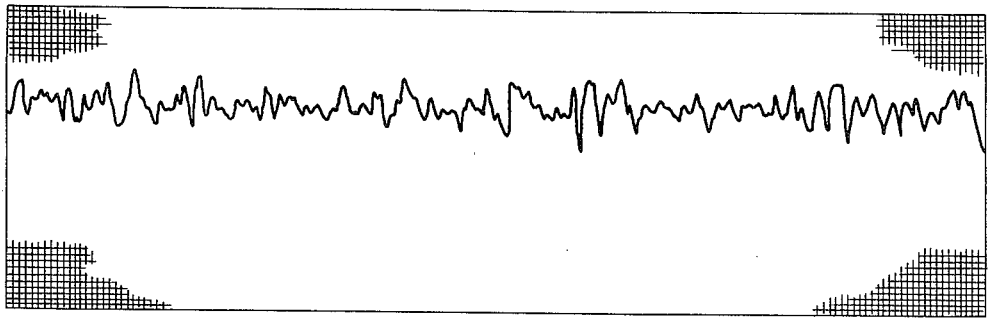
FIG. 12 is a similar actual brain wave pattern trace showing a person during a state of attention.

FIG. 12 corresponds somewhat to FIG. 7 in so far as it shows a relatively attentive state with occasional aberrations; FIG. 13 shows a generally attentive state with a few high amplitude aberrations. FIGS. 12 and 13 generally indicate good, if not excellent, attention characteristics. FIG. 14 also resembles FIG. 9 in so far as it shows alternating patters of high and low attention and a generally irregular pattern. FIG. 14 is typical of a brain wave trace which might be obtained from a child diagnosed as clinically hyperactive.

Typical of the apparatus which may also be used with the present invention in an attempt to coordinate sensory motor activity of body parts other than the eyes with eye movement control and control of attention span is the "Exer-Cor", an apparatus made by the Health and Education Service Corporation Division of the Flick-Reedy Company of Bensenville, Illinois. This device is a so-called homolateral and cross-lateral training device which has been known to be used in training students to improve their sensory motor coordination level.

According to the invention, when a subject who has difficulty in attending during reading is placed on the apparatus, and performs the exercises which are controlled by the machine, his brain wave pattern will almost immediately shift from a random pattern typical of inattention (such as that shown in FIGS. 10 and 11) into a pattern indicative of a state of high attention (FIG. 12 or 13). The use of such exercise apparatus is an alternative or supplement to performing the metronomically controlled exercises (squeezing a bag or ball, etc.) referred to in U.S. Pat. No. 4,078,319.

The "Exer-Cor" device has pads for receiving the knees and hands, and is mechanically arranged so that when a person correctly simulates a crawling movement calling for homolateral and cross-lateral muscle movements, the machine will "lock up" if the indicated movements are not made.

By homolateral is meant advancing the right hand and foot together, and by cross-lateral is meant advancing the right hand and left foot simultaneously.

Another apparatus which is useful with the present invention is a so-called voice stress analyzer. This instrument, which is of a known type and which has been used by those skilled in the art in so-called lie detector applications, detects the presence of physiological stress present in a person by analyzing the otherwise imperceptible variations in the audible characteristics of the human voice. According to present practice, the voice stress analyzer is based on the assumption that if the subject of the voice test is physiologically uncomfortable with some perceived situation during the time his voice is being analyzed, the analyzer will detect the existence of this stress. According to the invention, however, it has been found that such stresses occur naturally in students when they are under stress or other difficulty which does not relate to the truth or falsity of the subject under discussion.

Properly so called, the stress analyzer is just what the name implies, that is, it detects that a stressful situation is present in the subject. In reading or other learning situations, stress may arise as a result of even unconscious lapses out of an attentive state. Often, there is subconscious competition within an individual between attentive and non-attentive states, or in other cases, the stress may be merely physiologically stress resulting from an attempt to perform a task requiring a great deal of attention while the body itself is not physiologically capable of attaining an attentive state.

Consequently, according to the invention, it is more important to determine that stress is present than to determine the cause of it. Where stress is present, according to the invention, it can be reliably predicted that the test being given is not an accurate indicator of the ability of the subject, and the matter of applying therapy to such person can then be separately considered. The mechanism of using the voice stress analyzer includes having the student recite aloud what he is reading or studying, and monitoring the analyzer for indications of stress.

Another apparatus which is also useful in the practice of the invention is the so-called feed back dermograph. Such apparatus is an electrically operated unit for monitoring the electrical properties and activity of the skin of a subject. The so-called dermographic processes are processes of changes of skin conditions. Fluctuations in these functions relate closely to emotional arousal mechanisms. Typically, such apparatus detects the skin conductance level and the skin potential (voltage) level in a pre-determined area of the skin. Such apparatus will also determine skin conductance response and skin potential response, that is, the rapid momentary fluctuations of electrically measured skin characteristics.

Still another apparatus which is useful with the invention is a skin temperature recording and analyzing apparatus, which determines the dilation and constriction of blood vessels on or near the surface of the skin. In addition to the above, a so-called feed back electromyograph is sometimes used, and this apparatus determines the pattern of contraction and relaxation of skeletal muscles of the subject.

All of the instruments, including the EEG referred to elsewhere herein, are basically indicative of physiological conditions within the subject being tested and, as pointed out, indicate the presence of stress or other adverse psychological or physiological conditions which can be relieved or treated by appropriate therapy. As with the other instruments referred to herein, the use of these instruments includes establishment of base curves or characteristics, followed by comparison of these base characteristics with characteristics exhibited during the times learning is being attempted or tests are being administered.

Instruments of the type referred to herein and which have been successfully used in the practice of the invention include those made by Autogenic Systems, Inc., of Berkeley, Calif.

In view of the foregoing, the present invention consists, among other things, in the discovery that it is possible to organize a remedial reading program at a local school or clinic using largely existing material with the addition of only certain equipment, and additional training for the fifteen to thirty percent of the children which have heretofore not been considered amenable to progress within remedial reading classes.

Considered in its broadest state, the present invention comprehends monitoring a test subject while he is in a learning situation, establishing a set of base data for comparative purposes, studying the subject to determine the type of therapy which appears to promise success, discounting or revaluing test results given during periods when there are indications of inattention, and continuing the administration of reading and other learning training while monitoring continues, to determine the effectiveness of the therapy and to improve the clinical performance of the test subject. In the broadest sense, the therapy consists of treating the student, by exercise or dietary means, to achieve suppression or attenuation of excess alpha brain wave amplitudes and pattern variation during learning or testing.

In some cases, only limited therapy need be applied for a short time and in other instances, several forms of therapy must be administered and extensive training must be given. Even where the therapy discussed herein is not highly effective, the monitoring methods will almost always indicate that a physiological cause of reading difficulty is present so that such condition can be at least understood and studied further, rather than being ignored and permitting a student to be characterized by test results which are not indicative of his ability to read and understand.

It will thus be seen that the present invention provides a novel method and apparatus for monitoring attention and cognition, monitoring the effect of sensory motor, nutritional and other biochemical factors thereon, as well as therapeutic methods useful in teaching reading and other disciplines, said methods having a number of advantages and characteristics including those pointed out above and others which are inherent in the invention.

A preferred embodiment of the invention having been described by way of illustration, it is anticipated that changes to and modifications of, the described method and apparatus will occur to those skilled in the art and it is anticipated that such changes and modifications may be made without departing from the spirit of the invention or the scope of the appended claims.

APPENDIX

Bibliography

The following are merely illustrative articles dealing with trace mineral assays or analyses of hair.

1. Baumslag, N.; Petering, H. G. Trace metal studies in Bushman hair. Arch Environ Health 31(5):254–57, 1976.
2. Creason, J. P. et al. Trace elements in hair, as related to exposure in metropolitan New York. Clin Chem 21(4):603–12, 1975. Significant correlations within a single metropolitan area between trace element content of hair and exposure were found. Several metals increase and decrease together in the hair in agreement with trends reported for other human tissues.
3. Eatough, D. J. et al. Level of selected trace elements in human hair. First Human Hair Symposium, A. Brown, ed., p. 377–87, Medcom Press, 1975.
4. Greger, J. L. et al. Nutritional status of adolescent girls in regard to zinc, copper, and iron. Am. J. Clin. Nutr. 31(2):269–75, 1978. A survey of adolescent girls showed concentrations of zinc and copper in the hair were significantly correlated.
5. Kopito, L. E.; Shwachman, H. Alterations in the elemental composition of hair in some diseases. *The First Human Hair Symposium,* A. Brown, ed., p. 83–90, Medcom Press, 1975. An elevated concentration of potassium in relation to sodium was found in celias disease. Severely malnourished children also exhibited elevated potassium in hair. As the nutritional condition improved, the potassium concentration diminished and sodium increased until near normal ratios were reached. High levels of tightly-bound calcium was found in patients with geophagia and a much lower level was found in both male and female phenylketenuria patients.
6. Pihl, R. O.; Parkes, M. Hair element content in learning disabled children. Science 198)204–06, 1977. A discriminant function analysis showed that by using cadmium, cobalt, manganese, chromium and lithium determinations in hair analysis of learning disabled children, the learning disabled could be separated from normals with 98% accuracy.
7. Schroeder, H. A.; Nason, A. P. Trace element analysis in clinical chemistry. Clin. Chem. 17(6):461, 1971. Review of analyses of trace elements by blood, urine and hair. Analyses are applicable as diagnostic aids and indices for therapy in a number of clinical conditions. They will become more or less routine for many diseases in which primary or secondary abnormalities are manifest.

We claim:

1. A method of analyzing and modifying the behavioral response of a test subject displaying learning disability and of administering therapy for said disability, said method including the steps of monitoring the characteristic aplha brain wave pattern displayed by said subject during an attempt by said subject to attend to and understand written material, analyzing said pattern to determine the frequency of occurrence and duration of high amplitude alpha brain waves occurring in the subject, said high amplitude waves being those which are high in relation to the amplitude of alpha brain waves of a test subject displaying good attention characteristics and not characterized by a learning disability, said method further including the step of administering at least one therapeutic method selected from the group of therapeutic methods which includes print size variation reading therapy, sensory motor therapy and nutritional therapy in order to reduce said frequency of occurrence and said duration of said high amplitude alpha brain waves.

2. A method as defined in claim 1 which includes the further step of presenting written materials to said student so that said student can learn therefrom, said presentation of written materials being made during a time in which said occurrence frequency and duration of said high amplitude portions of said brain wave pattern have been reduced.

3. A method as defined in claim 1 wherein said therapeutic method is nutritional therapy and includes analyzing the amounts and relative proportions of nutrient minerals present in the test subject, and administering dietary therapy to normalize said amounts and ratios of said nutrient minerals present in said subject in relation to the amounts and ratios of such minerals present in test subjects not displaying learning disability.

4. A method as defined in claim 1 wherein said therapeutic method is print size variation reading therapy and comprises presentation to the test subject of printed material having an apparent type size much smaller than the type size of ordinary print, thereby causing individual letters and words within the printed material to lie within a decreased angular lateral span in relation to the angular lateral span of counterpart letters and words in normal type, and increasing said apparent type size only after said test subject has displayed a brain wave pattern characterized and a duration occurrence frequency and duration of said high amplitude alpha brain waves.

5. A method as defined in claim 1 in which said therapeutic method is nutritional therapy and includes administering at least one low molecular weight, simple L-amino acid to said test subject, and presenting written material to said test subject for study during the time said test subject is metabolizing said amino acid.

6. A method as defined in claim 1 wherein said therapeutic method is sensory motor therapy and includes training said student in the repetition of coordinated homolateral and cross-lateral arm and leg movements with the aid of a mechanical device adapted to assist said test subject in achieving such coordinated movements.

7. A method as defined in claim 1 wherein said therapeutic method is sensory motor therapy and includes training said student in the repetition of predetermined fine motor non-eye muscular movements in rhythm with coordinated eye movement sequences during the administration of training to said test subject.

8. A method as defined in claim 1 wherein said learning disability is a reading disability, wherein said written material comprises reading material, and where said therapeutic method includes both said print size variation reading therapy and said sensory motor therapy, said method also including the steps of periodically repeating said monitoring step and said therapy step at periodic intervals until said test subject has substantially reduced the effect of said learning disability.

9. A method as defined in claim 1 which further includes the administration of stress detection methods during said attempt by said subject to attend to and understand said written material.

10. A method as defined in claim 9 wherein said stress detecting methods include myographic methods, skin temperature detection methods, dermographic methods, including determination of skin conductance and skin potential levels, and voice stress analysis methods administered during oral reading.

11. A method of analyzing and modifying the behavioral response of a test subject attempting to attend to and understand written material, said method including the application of at least one analysis procedure to said test subject during said attempt, said procedure being selected from the group of analysis procedures which includes electroencelographic analysis, myographic analysis, skin temperature analysis, skin and conductivity and potential analysis, and voice stress analysis, observing the response pattern resulting from said analysis, comparing said response with a pattern generated by a test subject in a state of close attention, and modifying said response pattern in a test subject displaying a pattern indicating that said test subject is undergoing physiological stress, by administration to said subject of at least one therapeutic method selected from the group of therapeutic methods which includes print size variation reading therapy, sensory motor therapy and nutritional therapy.

12. A method of modifying the learning pattern of a subject displaying learning disability which includes the steps of determining a characteristic brain wave pattern of said subject during an attempt by said subject to attend to and understand written material, and, in the case of test subjects having a brain wave pattern characterized by alpha brain wave amplitudes which are undesirably high in relation to the alpha brain wave amplitudes displayed by a test subject not displaying learning disability, said method including the further step of achieving suppression of said undesirably high brain wave amplitudes by administering learning assistance therapy to the student, said assistance therapy including a therapeutic method from the group of methods which includes sensory motor therapy, nutritional therapy, and print size variation reading therapy, and subsequently presenting learning materials to said student when said undesirably high brain wave amplitudes have been suppressed.

13. A method of analyzing reading test scores taken from a plurality of subjects to whom reading tests have been previously administered, said method including the steps of determining the test scores achieved by each student in said previously administered test, subsequently administering reading tests to said plurality of test subjects whle taking an electroencephalographic alpha brain wave pattern trace of said student, determining the occurrence frequency and duration of high amplitude alpha brain waves, said high amplitude patterns being determined in relation to the amplitude characteristic of the brain wave pattern of a student in a condition of close attention, and retaining as reliable indicators of learning ability those test results which were achieved while said students displayed reduced occurrence frequency and duration of high amplitude alpha brain wave patterns and discarding as a reliable indicator of reading ability the results those tests administered during a time when the test subject was displaying at least either frequently occurring or long duration high amplitude alpha brain wave patterns.

14. A method of analyzing test scores and administering therapy to test subjects requiring reading improvement, said method including the analysis method as defined in claim 13 and further including the step of suppressing variations in the brain wave pattern of the subjects by administering at least one therapeutic procedure from the group of therapeutic procedures which includes sensory motor therapy, print size variation reading therapy and nutritional therapy.

15. A method as defined in claim 14 which includes the step of administering further tests when said therapeutic procedures have been effected to reduce the occurrence frequency and duration of said high amplitude alpha brain wave patterns in relation to the occurrence frequency and duration of said high amplitude alpha brain wave patterns previously manifested by said test subjects.

* * * * *

UNITED STATES PATENT AND TRADEMARK OFFICE
CERTIFICATE OF CORRECTION

PATENT NO. : 4,332,566
DATED : June 1, 1982
INVENTOR(S) : Conrad A. Mazeski and Ken Candelaria It is certified that error appears in the above—identified patent and that said Letters Patent is hereby corrected as shown below:

Column 3, line 33, delete the word "repeaably" and in place thereof, insert -- repeatably --;

line 67, after the word "fcund", please insert the word -- that --;

Column 4, line 13, delete the word "an", and in place thereof insert -- a --;

Column 7, line 45, delete the word "suject", and in place thereof, insert -- subject --;

Column 8, lines 29 and 30, please delete the words "showing a pattern trace";

Column 9, line 42, delete the word "show", and in place thereof insert -- shown --;

Column 11, line 51, delete the word "wo", and in place thereof insert -- who --;

12, line 5, delete the word "afew", and in place thereof insert -- a few --;

UNITED STATES PATENT AND TRADEMARK OFFICE
CERTIFICATE OF CORRECTION

Page 2 of 3

PATENT NO. : 4,332,566
DATED : June 1, 1982
INVENTOR(S) : Conrad Mazeski and Ken Candelaria It is certified that error appears in the above—identified patent and that said Letters Patent is hereby corrected as shown below:

Column 12, line 11, after the word "of", insert the word -- a --;

line 49, after the word "characteristic", delete the word "by", and in place thereof, insert -- of --;

Column 13, line 59, delete the word "intak", and in place thereof, insert -- intake --;

Column 16, line 47, delete the word "reponses" and in place thereof, insert -- responses --;

Column 18, line 31, delete the word "by" and in place thereof, insert the word -- of --;

Column 19, line 65, delete the word "physiologically" and in place thereof, insert -- physiological --;

Column 21, line 47, please italize the words "First Human Hair Symposium";

UNITED STATES PATENT AND TRADEMARK OFFICE
CERTIFICATE OF CORRECTION

PATENT NO. : 4,332,566

DATED : June 1, 1982

INVENTOR(S) : Conrad A. Mazeski and Ken Candelaria

It is certified that error appears in the above—identified patent and that said Letters Patent is hereby corrected as shown below:

Column 22, line 19, please delete the word "aplha" and in place thereof, insert -- alpha --;

Column 23, line 13, delete the word "administeration" and in place thereof, insert -- administration --;

Column 24, line 23, the word "whle" should be -- while --.

Signed and Sealed this

Sixteenth Day of November 1982

[SEAL]

Attest:

Attesting Officer

GERALD J. MOSSINGHOFF

Commissioner of Patents and Trademarks